United States Patent
Jung (10) Patent No.: US 12,178,681 B2
(45) Date of Patent: Dec. 31, 2024

(54) IMPLANT PACKAGING CONTAINER

(71) Applicant: Seoul Viosys Co., Ltd., Ansan-si (KR)

(72) Inventor: Hee Cheul Jung, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 1794 days.

(21) Appl. No.: 16/098,334

(22) PCT Filed: Apr. 26, 2017

(86) PCT No.: PCT/KR2017/004431
§ 371 (c)(1),
(2) Date: Nov. 1, 2018

(87) PCT Pub. No.: WO2017/191925
PCT Pub. Date: Nov. 9, 2017

(65) Prior Publication Data
US 2019/0159874 A1   May 30, 2019

(30) Foreign Application Priority Data
May 2, 2016   (KR) .................. 10-2016-0053953

(51) Int. Cl.
*A61C 8/00* (2006.01)
*A61C 19/02* (2006.01)
(Continued)

(52) U.S. Cl.
CPC .............. *A61C 8/0087* (2013.01); *A61C 8/00* (2013.01); *A61C 8/005* (2013.01); *A61C 19/02* (2013.01); *A61L 2/10* (2013.01); *A61L 2/26* (2013.01); *B65D 51/26* (2013.01); *B65D 81/28* (2013.01); *B65D 81/30* (2013.01); *A61C 2202/00* (2013.01)

(58) Field of Classification Search
None
See application file for complete search history.

(56) References Cited

U.S. PATENT DOCUMENTS 6,261,097 B1    7/2001  Schmutz et al.
9,168,570 B2   10/2015  Ogawa
(Continued)

FOREIGN PATENT DOCUMENTS

CN    102538383 B  * 12/2013
CN    201350228     11/2019
(Continued)

OTHER PUBLICATIONS

International Search Report mailed Aug. 4, 2017, in International Application No. PCT/KR2017/004431.
(Continued)

*Primary Examiner* — Andrew Smyth
(74) *Attorney, Agent, or Firm* — Oblon, McClelland, Maier & Neustadt, L.L.P.

(57) ABSTRACT

A dental implant packaging container including a main body having an inner wall defining a space for receiving a dental implant, a cap detachably coupled to one side of the main body, a securing portion mounted on the cap and configured to secure the dental implant inside the main body; a bottom portion coupled to the main body and facing the cap, and a main body reflector disposed on the inner wall of the main body and reflecting UV light emitted towards the cap.

11 Claims, 8 Drawing Sheets

(51) Int. Cl.
*A61L 2/10* (2006.01)
*A61L 2/26* (2006.01)
*B65D 51/26* (2006.01)
*B65D 81/28* (2006.01)
*B65D 81/30* (2006.01)

(56) References Cited

U.S. PATENT DOCUMENTS

| | | |
|---|---|---|
| 2013/0062535 A1 | 3/2013 | Park et al. |
| 2013/0167873 A1 | 7/2013 | Ogawa |
| 2013/0189642 A1 | 7/2013 | Ogawa |
| 2013/0264495 A1 | 10/2013 | Ogawa |

FOREIGN PATENT DOCUMENTS

| | | | |
|---|---|---|---|
| DE | 19544392 | 7/1996 | |
| JP | 2000-512195 A | 9/2000 | |
| JP | 3203603 U | 4/2016 | |
| KR | 20-2011-0008520 | 9/2011 | |
| KR | 10-1102993 | 1/2012 | |
| KR | 10-2013-0054357 | 5/2013 | |
| KR | 10-1445819 | 9/2014 | |
| KR | 10-1483431 | 1/2015 | |
| KR | 101483431 B1 * | 1/2015 | |
| KR | 10-1675508 | 11/2016 | |
| KR | 10-1688931 | 1/2017 | |
| WO | WO 2009/147166 A1 | 12/2009 | |
| WO | 2011/113568 | 9/2011 | |
| WO | WO-2011113568 A1 * | 9/2011 | ........... A61C 8/0012 |
| WO | 2016/198429 | 12/2016 | |

OTHER PUBLICATIONS

Extended European Search Report issued on Apr. 2, 2020 in European Patent Office 17792827.2.

Office Action issued Apr. 29, 2024, in corresponding European Patent Application No. 17 792 827.2, 6 pages.

* cited by examiner

IMPLANT PACKAGING CONTAINER

CROSS REFERENCE TO RELATED APPLICATION

This application is a National Stage Entry of International Application No. PCT/KR2017/004431, filed on Apr. 26, 2017, and claims priority from and the benefit of Korean Patent Application No. 10-2016-0053953, filed on May 2, 2016, each of which are hereby incorporated by reference for all purposes as if fully set forth herein.

BACKGROUND

Field

Exemplary embodiments of the invention relate generally to an implant packaging container and, more specifically, to an implant packaging container adapted to maintain a dental implant in a sterilized state before placement of the dental implant in the jawbone of a patient.

Discussion of the Background

A dental implant generally includes a fixture serving as a dental root, an abutment connected to the fixture, and a dental prosthesis seated on the abutment, and it is important to firmly fix the fixture of the dental implant, which is placed in the jawbone, to teeth during the implantation.

Although various metals and alloys have been developed as materials for the fixture, titanium (Ti) or Ti alloys are mainly used as materials for the fixture. Ti or Ti alloys have various advantages including easy machining, high biocompatibility with biological tissues, high mechanical strength, and biological inactivity. However, Ti or Ti alloys have a drawback in that a fixture formed of Ti or Ti alloys requires a long time for bonding with the bone upon implantation in the human body, and metal ions can be dissolved in the body after a long time after implantation.

In order to overcome such drawbacks, several techniques have been developed for enhancing bone bonding through surface treatment on the surface of Ti or an Ti alloy. Specifically, the rate and quality of bone bonding are closely related to the surface properties and chemical composition of the fixture, such as surface adjustment, surface roughness, hydrophilicity, and the like. In particular, it is known in the art that fixtures having highly hydrophilic surfaces are advantageous in interaction with biological solutions, cells, and tissues.

Further, titanium on the surface of the fixture is known to be oxidized to form an oxide layer ($TiO_2$) and the titanium oxide layer is stable in a living body and exhibits good biological compatibility and positive features in reaction with cells, and a dental implant subjected to oxidation treatment has better bone bonding with the bone than a dental implant subjected only to machining.

However, the oxide layer formed on the surface of the fixture can suffer from deterioration in hydrophilicity after a predetermined period of time, as compared with the oxide layer immediately formed thereon. Therefore, the dental implant is typically irradiated with UV light before packaging or further irradiated with UV light using a UV irradiator before placement of the dental implant in order to improve hydrophilicity of the fixture.

However, irradiation of the dental implant with UV light before packaging can cause significant deterioration in hydrophilicity of the fixture after a predetermined period, thereby causing patient pain upon implantation, and use of the UV irradiator can cause contamination of the dental implant in the course of taking the dental implant out of a packaging container thereof.

Therefore, there is a need for development of an effective method or a packaging container for improving hydrophilicity of the fixture in a sterilized state before placement of the dental implant in the jawbone of a patient.

The above information disclosed in this Background section is only for understanding of the background of the inventive concepts, and, therefore, it may contain information that does not constitute prior art.

SUMMARY

An implant packaging container according to an exemplary embodiment can conveniently and efficiently improve hydrophilicity of a fixture before implantation of a dental implant in the jawbone of a patient to reduce patient pain through improvement in biological compatibility of the fixture with living tissue, while reducing a time for bonding with the bone upon implantation.

An implant packaging container according to an exemplary embodiment also maintains a dental implant in a sterilized state before placement of the dental implant in the jawbone of a patient.

Additional features of the inventive concepts will be set forth in the description which follows, and in part will be apparent from the description, or may be learned by practice of the inventive concepts.

A dental implant packaging container according to an exemplary embodiment includes a main body having an inner wall defining a space for receiving a dental implant, a cap detachably coupled to one side of the main body, a securing portion mounted on the cap and configured to secure the dental implant inside the main body, a bottom portion coupled to the main body and facing the cap, and a main body reflector disposed on the inner wall of the main body and reflecting UV light emitted towards the cap.

The dental implant packaging container may further include a dental implant configured to be mounted on the main body, the dental implant may include an abutment connector configured to be coupled to the securing portion, an abutment, and a fixture, in which the dental implant is configured to be disposed between the securing portion and the bottom portion.

The bottom portion may be detachable from the main body, and UV light may configured to be emitted into the main body, with the bottom portion removed from the main body.

The securing portion may include a securing portion reflector configured to reflect UV light emitted into the main body from the bottom portion.

The main body reflector may be configured to reflect UV light having passed through the bottom portion.

The main body reflector may include at least one of aluminum materials, a fluorine-based polymer, SUS, glass, ceramic materials, and combinations thereof.

The main body reflector may include aluminum or polytetrafluoroethylene.

The main body reflector may have a thickness of 0.003 mm to 50 mm.

A length of the main body reflector may be at least one third the length of the fixture of the dental implant.

An inner space of the main body may gradually narrow from the bottom portion to the cap.

The main body reflector may include a reflective material.

The reflective material layer may be coated on the inner wall of the main body.

The main body reflector may include a reflective tape attached to the main body.

The main body reflector may have a barrel-shape and may be inserted into the main body.

The dental implant packaging container may further include at least one fastener configured to secure the main body reflector to the inner wall of the main body.

The dental implant packaging container may further include a pedestal disposed between the main body reflector and the bottom portion inside the main body to place the main body reflector thereon.

The dental implant packaging container may further include a UV light source disposed on the bottom portion and configured to emit UV light into the main body.

When A indicates the shortest distance from the main body reflector to the dental implant and B indicates the shortest distance from the UV light source to the dental implant, A and B may satisfy relationships of 0.1 mm≤A≤50 mm and 0.7≤B/A≤1.

The main body reflector may be spaced apart from the cap and the bottom portion.

The main body reflector may be disposed to overlap only a portion of the dental implant.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Figure 1:
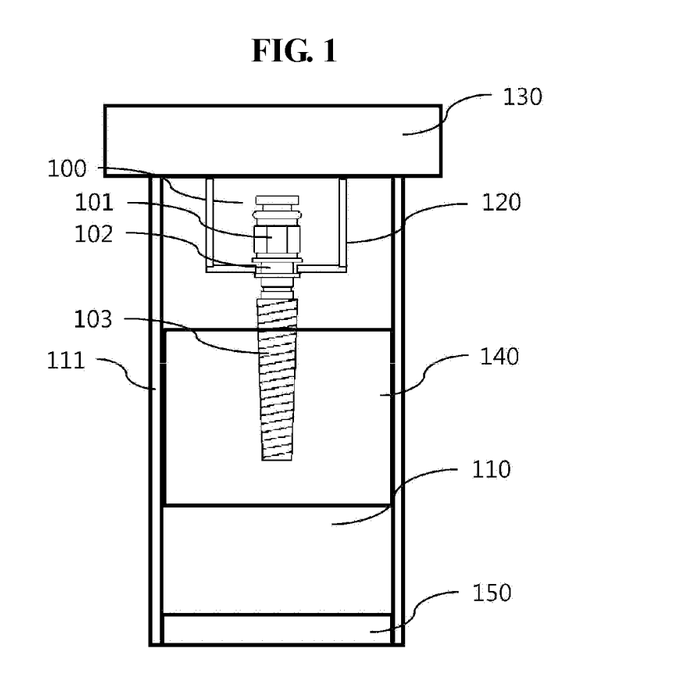
FIGS. 1, 2, 3, 4, and 5 are cross-sectional views of an implant packaging container according to exemplary embodiments.
Figure 2:
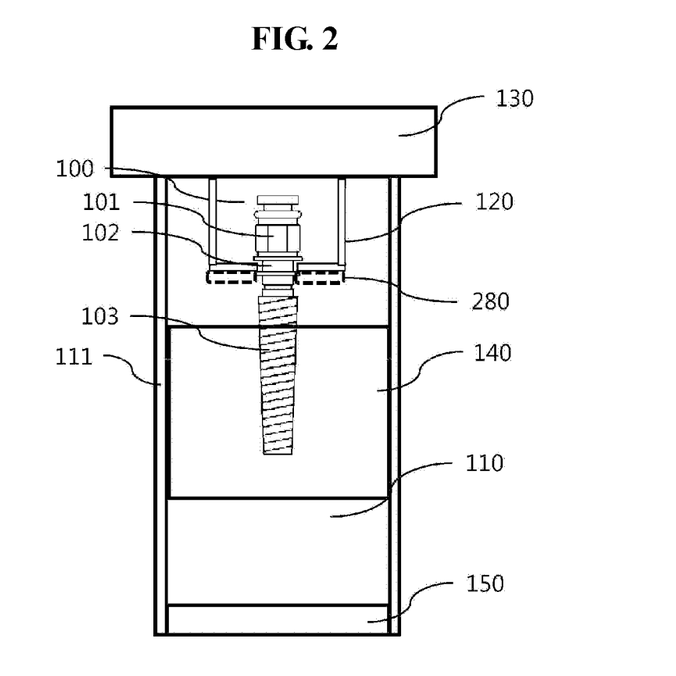
Figure 3:
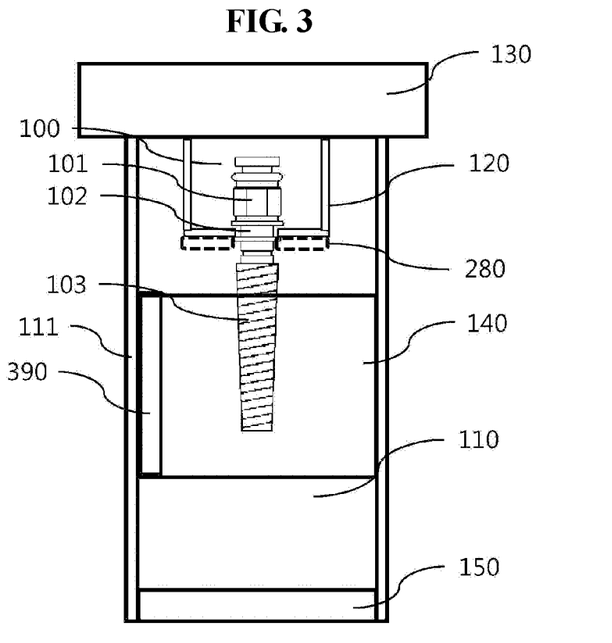
Figure 4:
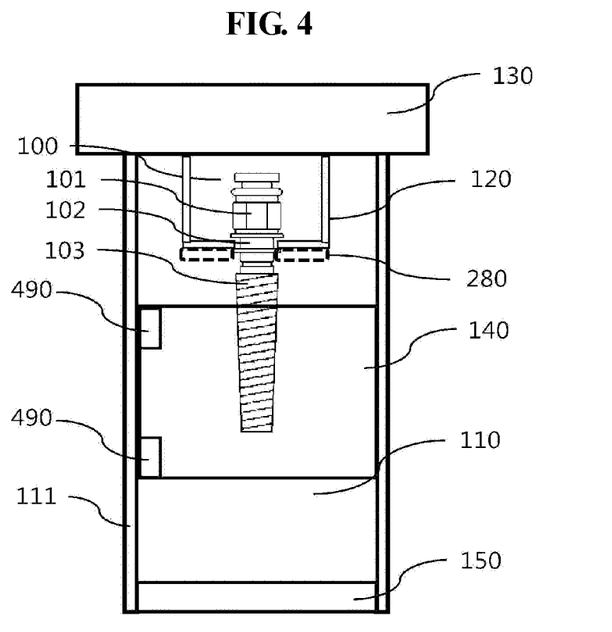

FIG. 1 and FIG. 2 are cross-sectional views of an implant packaging container according to exemplary embodiments.

Referring to FIG. 1, the implant packaging container according to an exemplary embodiment includes a main body 110 having an inner wall 111 defining a space for receiving a dental implant, a cap 130 detachably coupled to one side of the main body 110, a securing portion 120 securing a location of the dental implant inside the main body 110, a bottom portion 150 coupled to the main body 110 to face the cap 130, and a main body reflector 140 disposed on an inner wall of the main body 110 and reflecting UV light emitted from near the bottom portion 150.

The main body 110 is not limited to a particular shape and may have a polygonal barrel shape or a cylindrical shape. Preferably, the main body 110 has a cylindrical shape so as to allow the entirety of a dental implant 100 received in the packaging container may be irradiated with UV light reflected by the reflector 140. In addition, although the main body 110 may have any diameter and length so long as a typical dental implant can be received in the main body, the main body 110 may have a length of 10 mm to 30 mm and a diameter of 4 mm to 20 mm in consideration of reflection efficiency and economic feasibility. The main body 110 may be formed of a transparent material to allow the dental implant 100 received therein to be observed from the outside.

The cap 130 may be detachably coupled to one side of the main body 110. The securing portion 120 extending into the main body 110 may be mounted on the cap 130 and may be coupled to an abutment connector 102 of the dental implant 100. Here, inside the implant packaging container, the dental implant 100 may be secured by the securing portion 120 such that a fixture 103 of the dental implant 100 faces the bottom portion 150 and a mount 101 faces the cap 130.

Accordingly, in the implant packaging container, the dental implant 100 is mounted on the securing portion 120 extending from the cap 130, and the main body 110 is coupled to the cap 130 to receive the dental implant 100 in the implant packaging container for storage or transfer of the dental implant 100.

Referring to FIG. 2, the securing portion 120 according to an exemplary embodiment may include a securing portion reflector 280 adapted to reflect UV light emitted into the main body 110 from the bottom portion 150. Since the fixture 103 of the dental implant includes threads and valleys repeatedly arranged in a spiral shape, a region of the fixture 103 may not be irradiated with UV light when UV light is emitted from the bottom portion 150 toward the cap 130 in only one direction.

As such, the implant packaging container according to an exemplary embodiment further includes the securing portion reflector 280, thereby allowing UV light to be emitted not only from the bottom portion 150 toward the cap 130 but also from the cap 130 toward the bottom portion 150. With this structure, the implant packaging container allows the entirety of the fixture 103 of the dental implant 100 to be uniformly irradiated with UV light before placement of the dental implant in the jawbone of a patient, thereby conveniently and efficiently improving hydrophilicity of the fixture 103 to reduce patient pain through improvement in biological compatibility of the fixture 103 with living tissue while reducing a time for bonding with the bone upon implantation.

The bottom portion 150 may be coupled to the main body in an opposite direction to the cap 130, may be formed of a transparent material to allow UV light to pass therethrough, and may be detachably coupled to the main body 110.

As such, in some exemplary embodiments, the bottom portion 150 may be detachably coupled to the main body 110 and a UV irradiator may be coupled to the main body at the opposite side of the cap 130 after detachment of the bottom portion 150 from the main body 110, thereby allowing the interior of the main body 110 to be irradiated with UV light emitted from the UV irradiator.

Alternatively, the bottom portion 150 may be formed of a transparent material to allow UV light to pass therethrough and the UV irradiator may be disposed at the opposite side of the cap 130 without removing the bottom portion, thereby allowing the interior of the main body 110 to be irradiated with UV light emitted from the UV irradiator.

The implant packaging container may include the main body reflector 140 on the inner wall of the main body 110 to emit UV light emitted from near the bottom portion 150.

The main body reflector 140 may reflect UV light having passed through the bottom portion 150, and may include at least one selected from the group consisting of aluminum materials, a fluorine-based polymer, SUS, glass, ceramic materials, and combinations thereof. The fluorine-based polymer may include polytetrafluoroethylene (PTFE), polyvinyl fluoride (PVF), polyvinylidene fluoride (PVDF), polychlorotrifluoroethylene (PCTFE), fluorinated ethylene propylene (FEP), ethylene tetrafluoroethylene (ETFE), ethylene chlorotrifluoroethylene (ECTFE), perfluoropolyether (PFPE), and the like. Preferably, the main body reflector 140 is formed of aluminum or polytetrafluoroethylene.

The main body reflector 140 may have a thickness of 300 nm to 5 cm. If the thickness of the main body reflector 140 is less than 300 nm, the main body reflector 140 can have a significantly low reflectivity with respect to UV light, and if the thickness of the main body reflector 140 exceeds 5 cm, the volume of the implant packaging container increases too much, thereby reducing economic feasibility.

The main body reflector 140 may have a length that is one third the length of the fixture 103 of the dental implant received in the main body. If the length of the main body reflector 140 is less than one third the length of the fixture 103, it is difficult for the entirety of the fixture 103 to be uniformly irradiated with UV light emitted into the main body 110.

Figure 6:
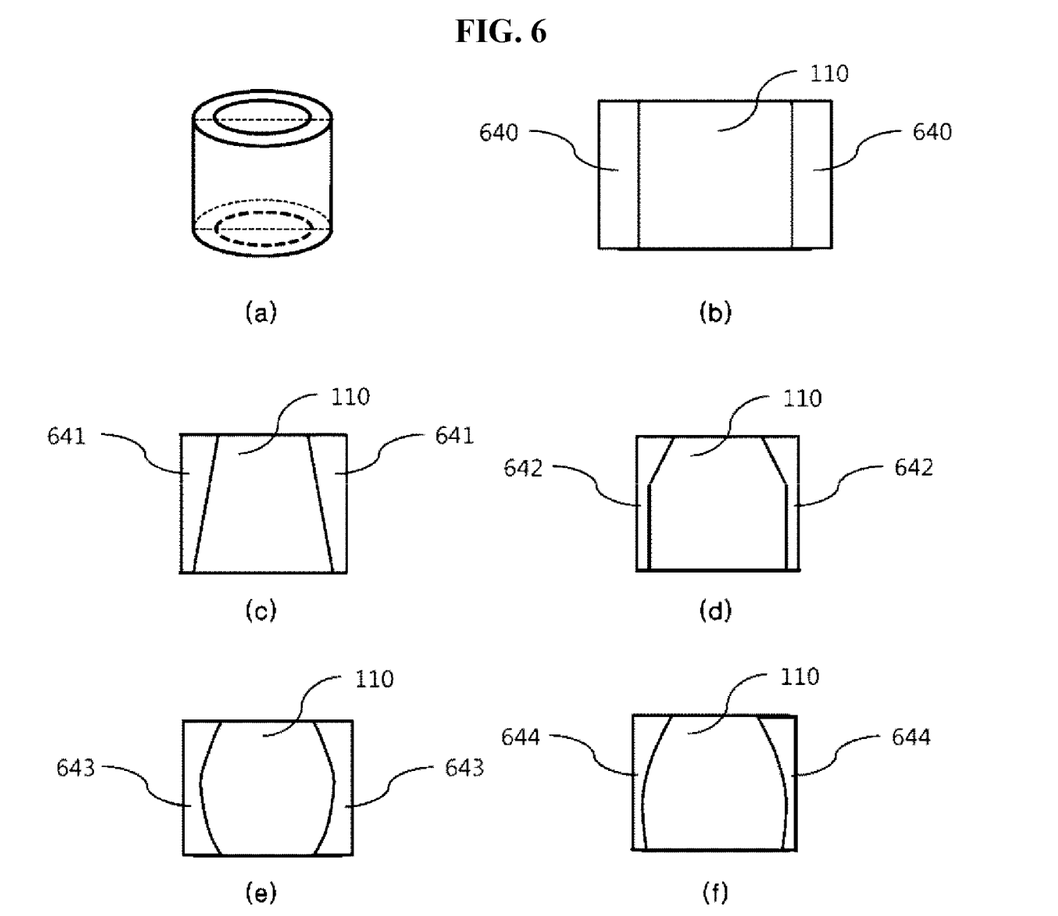
FIG. 6(a) is a perspective view of a main body and a main body reflector of the implant packaging container according an exemplary embodiment.
FIGS. 6(b), 6(c), 6(d), 6(e), and 6(f) are cross-sectional views of the main body of the implant packaging container of FIG. 6(a).

FIG. 6(a) is a perspective view of the main body 110 and the main body reflector 140 of the implant packaging container according to an exemplary embodiment, and FIG. 6(b) to FIG. 6(f) are cross-sectional views of the main body 110 of the implant packaging container shown in FIG. 6(a).

Referring to FIG. 1 and FIG. 6(a) to FIG. 6(f), each of main body reflectors 640, 641, 642, 643, 644 (as shown as 140 and 111 in FIG. 1) according to exemplary embodiments may include an inner wall region defining an inner space of the main body 110. Referring to FIGS. 6(b) to 6(f), at least a portion of an inner space of the main body 110 according to exemplary embodiments gradually narrows from the bottom portion 150 to the cap 130 to improve reflection efficiency such that the entirety of the fixture 103 of the dental implant can be irradiated with UV light emitted from the bottom portion 150 towards the cap 130 inside the main body 110.

Each of the main body reflectors 640, 641, 642, 643, 644 according to exemplary embodiments may be realized by the main body 110 formed of a reflective material. Specifically, the main body 110 or the inner wall 111 of the main body may be formed of a reflective material. In this case, it is possible to eliminate coating or deposition of a separate reflective material onto the inner wall 111 of the main body.

Alternatively, the main body reflector 140 may be realized by a reflective material layer coated onto the inner wall 111 of the main body or an outer surface thereof. That is, when the main body 110 or the inner wall 111 of the main body 110 is formed of a UV light transmittable material, the reflective material layer may be coated on the outer surface of the main body 110. Coating of the reflective material layer may be performed by any method known in the art, for example, dipping, spraying, electro-deposition, blasting, spread coating, and the like.

When the main body reflector 140 is provided to the inner wall 111 of the main body, the main body 110 is not necessarily formed of the UV light transmittable material and may be formed of a UV absorbable or reflective material. As such, in the implant packaging container according an exemplary embodiment, the main body 110 is not necessarily formed of the UV light transmittable material, thereby enabling reduction in manufacturing costs.

Alternatively, the main body reflector 140 may be realized by a reflective tape that can be bonded to the main body 110. Specifically, when the main body 110 or the inner wall 111 of the main body 110 is formed of the UV light transmittable material, the reflective tape may be bonded to the surface of the main body 110.

According to some exemplary embodiments, the main body reflector 140 may be a barrel-shaped reflector inserted into the main body 110.

In these exemplary embodiments, referring to FIG. 3, FIG. 4, FIG. 9 and FIG. 10, the implant packaging container may further include at least one fastener 390, 490, 990, and 1090 adapted to secure the main body reflector 140 (or 740) to the inner wall 111 (or 711) of the main body.

Figure 5:
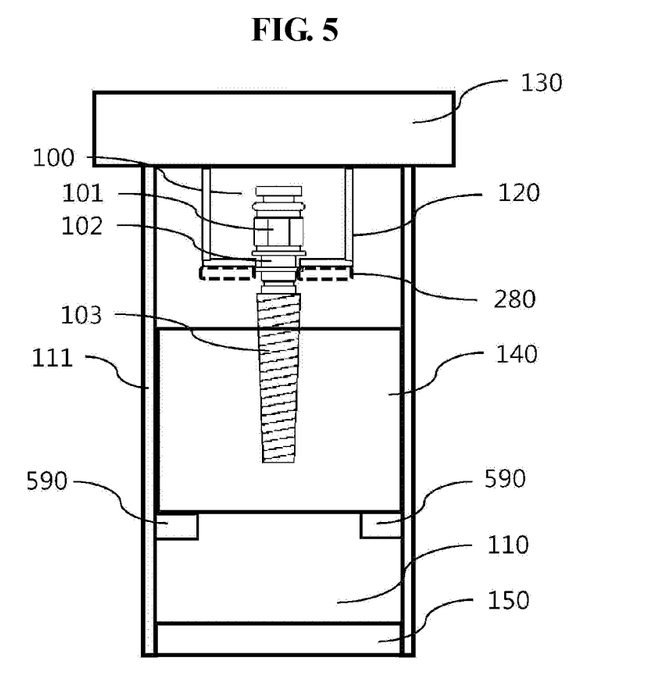
Figure 11:
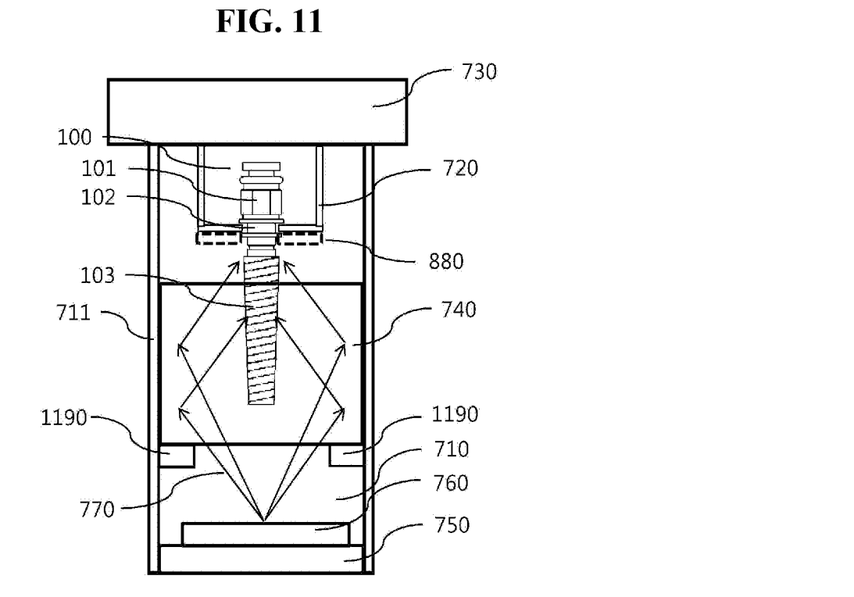

In addition, referring to FIG. 5 and FIG. 11, the implant packaging container may further include a pedestal 590 (or 1190) disposed between the main body reflector 140 (or 740) and the bottom portion 150 (or 750) inside the main body 110 (or 710) to place the barrel-shaped main body reflector 140 (or 740) thereon.

FIG. 7 to FIG. 11 are cross-sectional views of an implant packaging container according to exemplary embodiments.

The implant packaging container of FIGS. 7 to 11 is substantially identical to the implant packaging container of FIGS. 1 to 5, in that the implant packaging container includes a main body 710 including an inner wall 711 defining a space for receiving a dental implant 100, a cap 730 detachably coupled to one side of the main body 710, a securing portion 720 securing a location of the dental implant 100 inside the main body 710, a bottom portion 750 coupled to the main body 710 to face the cap 730, and a main body reflector 740 disposed on an inner wall 711 of the main body 710 and reflecting UV light 770 emitted into the main body. The implant packaging container according to exemplary embodiments may adopt the components of the implant packaging container described with reference to FIGS. 1 to 5.

In addition, the implant packaging container has the thickness, length, shape, and material of the main body reflector 740 and a connection relationship between the main body 710 and the main body reflector 740 substantially the same as those of the implant packaging container of FIGS. 1 to 6, and further includes a fastener 990 (or 1090) and a pedestal 1190.

Thus, the following description will focus on a connection relationship between a UV light source 760, the bottom portion 750, and a current supplier among the components of the implant packaging container.

Figure 7:
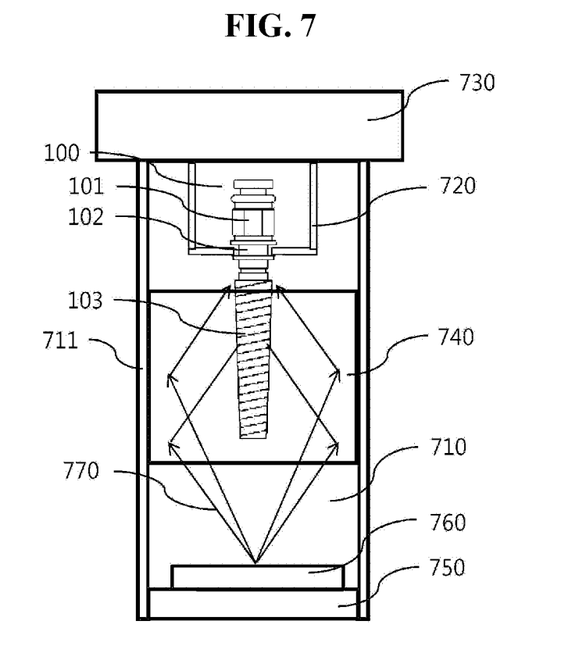
FIGS. 7, 8, 9, 10, and 11 are cross-sectional views of an implant packaging container according to exemplary embodiments.
Figure 8:
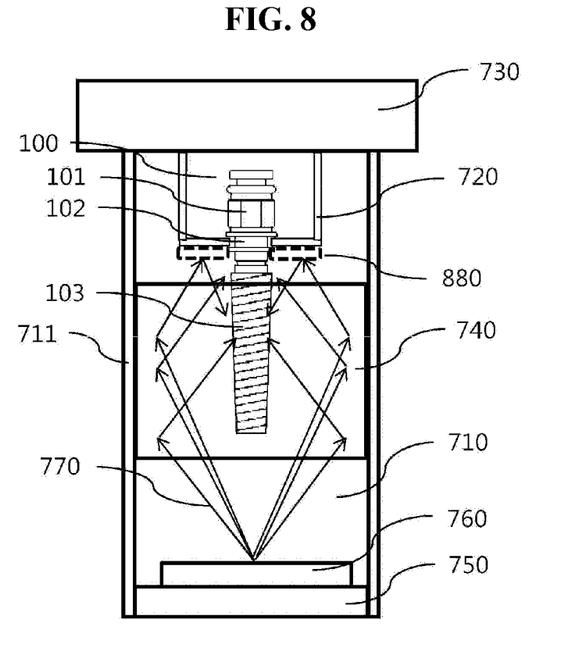
Figure 9:
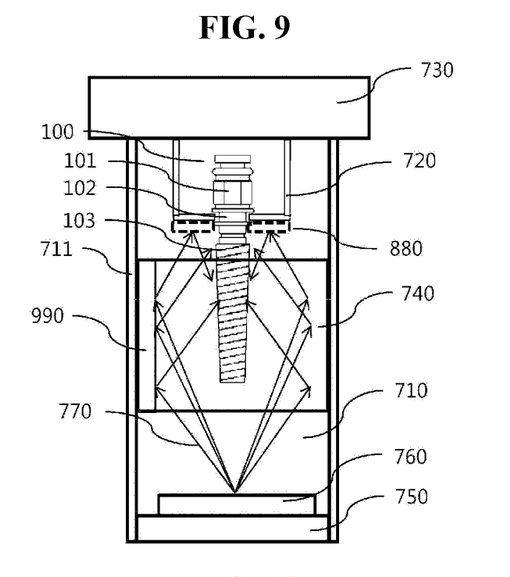
Figure 10:
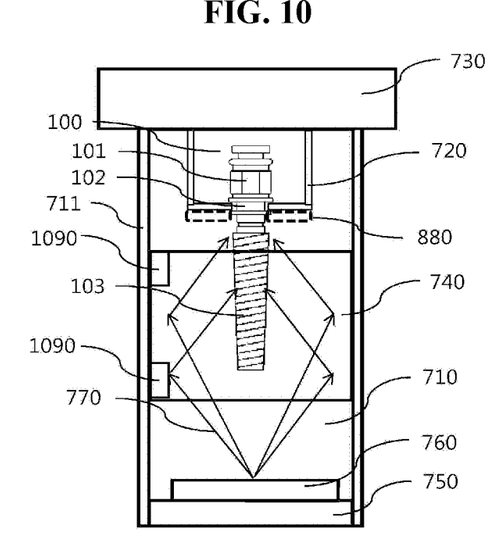

The implant packaging container according to an exemplary embodiment further includes the UV light source 760 adapted to emit UV light into the main body 710. The UV light source 760 may be mounted on the bottom portion 750. The bottom portion 750 on which the UV light source 760 is mounted may be realized by a printed circuit board (PCB) or may include the PCB.

Figure 12:
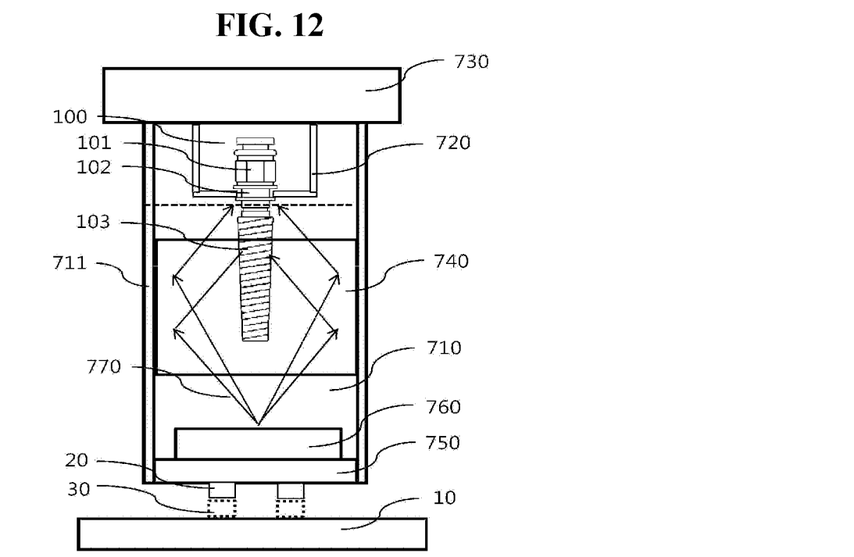
FIG. 12 to FIG. 13 are cross-sectional views illustrating a coupled state of connection terminals of the implant packaging container according to exemplary embodiments.
Figure 13:
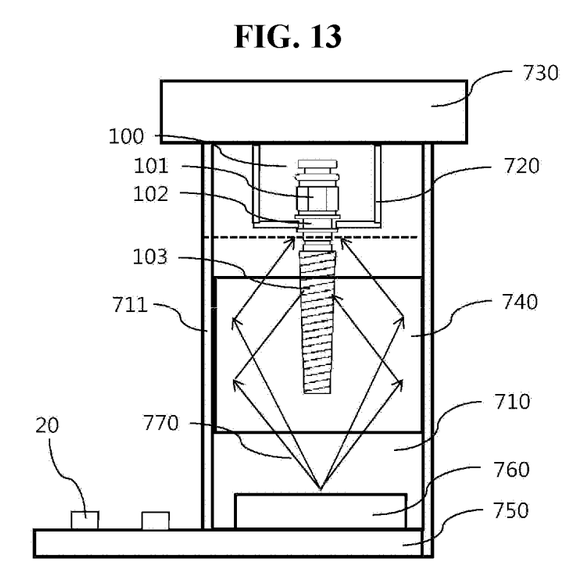

FIG. 12 and FIG. 13 are cross-sectional views illustrating a coupled state of connection terminals of the implant packaging container according to exemplary embodiments.

Referring to FIG. 12, the bottom portion 750 may include a first connection terminal 20 for connection to a current supplier 10. As shown in FIG. 12, the first connection terminal 20 may be formed on a lower surface of the bottom portion 750. With this structure, when the implant packaging container is placed on the current supplier 10, the first connection terminal 20 is connected to a second connection terminal 30 of the current supplier 10 to operate the UV light source 760.

Referring to FIG. 13, although the bottom portion 750 according to this exemplary embodiment is similar to the bottom portion 750 shown in FIG. 12, the bottom portion 750 extends outside the main body 710 and the first connection terminal 20 is formed on an upper surface of the bottom portion 750. The first connection terminal 20 may be electrically connected to the current supplier 10 through various connection structures.

Although the arrangement of the connection terminal is descried with reference to FIG. 12 and FIG. 13, it should be understood that the inventive concepts are not limited to the connection terminals shown in FIG. 12 and FIG. 13, and may be modified into various shapes and the first connection terminal 20 may be connected to the current supplier 10 having various shapes to allow the dental implant 100 received in the implant packaging container to be irradiated with UV light 770.

The UV light source 760 may emit UV light having a wavelength of 200 nm to 380 nm, preferably 250 nm to 350 nm, to improve hydrophilicity of the fixture 103 and a sterilization effect.

In addition, although hydrophilicity of the fixture 103 and the sterilization effect are improved with increasing light output of the UV light source 760, it is desirable that an electric current of 0.01 A to 2 A and a voltage of 2V to 20V be used in consideration of light output generation efficiency.

When A indicates the shortest distance from the main body reflector to the dental implant and B indicates the shortest distance from the UV light source to the dental implant, A and B may be set to satisfy relationships of 0.1 mm≤A≤50 mm and 0.7≤B/A≤1.

If B/A is less than 0.7, the fixture 103 can be damaged or suffer from deterioration in reflection efficiency due to contact between the UV light source 760 and the fixture 103, and if B/A exceeds 1, hydrophilicity of the fixture 103 cannot be sufficiently secured due to an excessively long distance between a portion near the abutment connector 102 of the fixture 103 and the UV light source 760.

According to exemplary embodiments, the implant packaging container is provided with a main body reflector inside a main body to allow a dental implant, particularly, the overall region of a fixture of the dental implant, to be uniformly irradiated with UV light. The implant packaging container may additionally include a cap reflector to allow the entirety of the fixture of the dental implant to be uniformly irradiated with UV light.

According to exemplary embodiments, the implant packaging container is provided with a UV light source inside the main body to prevent the dental implant from being exposed outside for UV irradiation, thereby maintaining the dental implant in a sterilized state before placement of the dental implant in the jawbone of a patient. In addition, including the UV light source inside the main body may allow the container to be formed of a UV transmittable material.

According to exemplary embodiments, the implant packaging container allows the entirety of the fixture of the dental implant to be uniformly irradiated with UV light through control of the shapes and lengths of the reflectors and the vertical shortest distance from the UV light source to the dental implant.

Accordingly, the implant packaging container according to exemplary embodiments allows the entirety of the fixture of the dental implant to be uniformly irradiated with UV light before placement of the dental implant in the jawbone of a patient, thereby conveniently and efficiently improving hydrophilicity of the fixture to reduce patient pain through improvement in biological compatibility of the fixture with living tissue while reducing a time for bonding with the bone upon implantation and maintaining the dental implant in a sterilized state immediately before placement of the dental implant in the jawbone of a patient.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

The invention claimed is:

1. A dental implant package container comprising:
   a main body having an inner wall defining a space for receiving a dental implant;
   a cap detachably coupled to one side of the main body;
   a secure region mounted on the cap and configured to secure the dental implant inside the main body;
   a bottom region coupled to the main body and facing the cap;
   a secure region reflector disposed on a lower surface of the secure region facing the bottom region; and
   a UV light reflector disposed on the inner wall of the main body and reflecting UV light emitted into the main body,
   wherein a length of the UV light reflector is at least one third a length of a fixture of the dental implant.

2. The implant package container according to claim 1, further comprising a dental implant configured to be mounted on the main body, the dental implant comprising an abutment connector configured to be coupled to the secure region, an abutment, and the fixture,
   wherein the dental implant is configured to be disposed between the secure region and the bottom region.

3. The implant package container according to claim 1, wherein the UV light reflector is configured to reflect UV light having passed through the bottom region.

4. The implant package container according to claim 1, wherein the UV light reflector comprises at least one of aluminum materials, a fluorine-based polymer, SUS, glass, ceramic materials, and combinations thereof.

5. The implant package container according to claim 4, wherein the UV light reflector aluminum or polytetrafluoroethylene.

6. The implant package container according to claim 1, wherein the UV light reflector has a thickness of 0.003 mm to 50 mm.

7. The implant package container according to claim 1, wherein the UV light reflector includes a reflective material layer.

8. The implant package container according to claim 7, wherein the reflective material layer is coated on the inner wall of the main body.

9. The implant package container according to claim 7, wherein the reflective material layer comprises a reflective tape attached to the main body.

10. The implant package container according to claim 1, wherein the UV light reflector is spaced apart from the cap and the bottom region.

11. The implant package container according to claim 10, wherein the UV light reflector is disposed to overlap only a region the dental implant.

\* \* \* \* \*